United States Patent
Keinan et al.

(12)

(10) Patent No.: US 6,440,710 B1
(45) Date of Patent: Aug. 27, 2002

(54) ANTIBODY-CATALYZED DEUTERATION, TRITIATION, DEDEUTERATION OR DETRITIATION OF CARBONYL COMPOUNDS

(75) Inventors: Ehud Keinan, Timrat; Avidor Shulman, Kiryat Tivon, both of (IL)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/208,381

(22) Filed: Dec. 10, 1998

(51) Int. Cl.[7] .............................. C12P 7/26; C12P 7/24; C07K 16/00; C12N 9/00; C12N 5/16
(52) U.S. Cl. .................... 435/148; 435/147; 435/188.5; 435/345; 435/346
(58) Field of Search ................................ 435/147, 148, 435/188.5, 345, 346

(56) References Cited

U.S. PATENT DOCUMENTS 5,733,757 A    3/1998   Barbas et al. ............... 435/148

OTHER PUBLICATIONS

Efficient Aldolase Catalytic Antibodies That Use the Enamine Mechanism of Natural Enzymes; By Jurgen Wagner, Richard A. Lerner, Carlos F. Barbas; Science * vol. 270 * Dec. 15, 1995.

*Primary Examiner*—David M. Naff
(74) *Attorney, Agent, or Firm*—Mark M. Friedman (57) ABSTRACT

Methods are provided for deuteration, tritiation, dedeuteration or detritiation of a carbonyl compound. A catalytic antibody that catalyzes an aldol addition reaction is contacted with a carbonyl compound to exchange at least one hydrogen atom of the carbonyl compound with a deterium or tritium atom of an isotopically enriched water molecule, or to exchange at least one deuterium or tritium atom of the carbonyl compound with a hydrogen atom. The aldol addition reaction may be between an aliphatic ketone donor and an aldehyde acceptor. Isotopically enriched water molecules include deuterium hydrogen oxide, dideuterium oxide, tritium hydrogen oxide, ditritium oxide and deuterium tritium oxide. The catalytic antibody may be that secreted by hybridoma 38C2 (ATCC HB 12005) or 33F12 (ATCC HB 12004).

15 Claims, 5 Drawing Sheets

ANTIBODY-CATALYZED DEUTERATION, TRITIATION, DEDEUTERATION OR DETRITIATION OF CARBONYL COMPOUNDS

FIELD AND BACKGROUND OF THE INVENTION

The present invention relates to a catalytic antibody and, more particularly, to a catalytic antibody effective in deuteration or tritiation of carbonyl compounds.

Deuterium- and tritium-labeled organic compounds have become increasingly important for the role they play in structure determination, mechanistic studies, elucidation of biosynthetic pathways and in biochemical studies. One of the most commonly used deuteration/tritiation methods is the acid or base-catalyzed exchange of protons α to a carbonyl function with $D_2O$. Unfortunately, the fairly strenuous aqueous conditions required to complete this exchange are incompatible with substrates that contain acid/base-sensitive functional groups (5, 6). These difficulties have inspired much activity and innovation at the level of process engineering (7). Deuteration or tritiation of aldehydes is a particularly difficult task because most aldehydes are incompatible with both basic and acidic conditions required for the exchange reaction (8). The use of amine catalysts that form intermediate enamines could represent a solution to this problem. This approach, however, is applicable only in rare cases where the enamine is sufficiently stable in water (9).

There is thus a widely recognized need for, and it would be highly advantageous to have, a catalytic antibody effective in deuteration or tritiation of carbonyl compounds.

Enzymes are fascinating tools in synthetic organic chemistry mainly due to their high levels of catalytic efficiency under mild reaction conditions (1). While antibodies have been shown to catalyze a remarkable range of chemical reactions with impressive rates (2), the question remains whether these biocatalysts, which are evolved over a few weeks time, would ever exhibit the same efficiency of highly evolved natural enzymes (3).

Here it is shown that there is no fundamental limit to the efficiency of antibody catalysis in terms of rate enhancement and turnover numbers.

Specifically it is reported herein that antibody 38C2 (4) catalyzes the deuterium exchange reaction with a variety of ketones and aldehydes. The catalytic rates ($k_{cat}$) and rate-enhancement values ($k_{cat}/k_{un}$) represent the highest values ever observed with catalytic antibodies. Such values are reminiscent of the efficiency of many natural enzymes.

SUMMARY OF THE INVENTION

While reducing the present invention to practice it was found that antibody 38C2 catalyzes a deuterium exchange reaction with a variety of ketones and aldehydes. All reactions were carried out in $D_2O$ under neutral conditions (pD 7.4). The exchange reaction was followed either by mass spectrometry (GCMS) or by $^1H$-NMR. In all cases the deuterium exchange reaction followed Michaelis-Menten kinetics and was effectively inhibited by acetylacetone. In addition to the regio- chemo- and enantioselectivity of these reactions, the catalytic rates ($k_{cat}$) and rate-enhancement values ($k_{cat}/k_{un}$) represent the highest values ever observed with catalytic antibodies. The observed regioselectivity is consistent with the formation of a protonated Schiff base intermediate at the lysine residue in the antibody active site followed by a reversible rearrangement to the corresponding enamine.

Thus, according to the present invention there is provided a method of deuteration or tritiation of a carbonyl compound comprising the step of contacting the carbonyl compound with a catalytic antibody being capable of catalyzing an aldol addition reaction in a presence of an aqueous solution enriched with an isotopically enriched water molecule to thereby exchange at least one hydrogen atom in the carbonyl compound with a deuterium or tritium atom.

According to further features in preferred embodiments of the invention described below, the isotopically enriched water molecule is selected from the group consisting of deuterium hydrogen oxide, dideuterium oxide, tritium hydrogen oxide, ditritium oxide and deuterium tritium oxide.

According to still further features in the described preferred embodiments the catalytic antibody being capable of catalyzing the aldol addition reaction between an aliphatic ketone donor and an aldehyde acceptor.

According to still further features in the described preferred embodiments the catalytic antibody is characterized by having a lysine with an ε-amino group.

According to still further features in the described preferred embodiments the catalytic antibody is subject to inhibition with a molecule containing a β-dicarbonyl group by formation of a complex between the β-dicarbonyl group and the ε-amino group of the lysine of the catalytic antibody.

According to still further features in the described preferred embodiments the complex is selected from the group consisting of a stable covalent vinylogous amide, a conjugated enamine and a Schiff base.

According to still further features in the described preferred embodiments the catalytic antibody controls the diastereofacial selectivity of the aldol addition reaction in both Cram-Felkin and anti-Cram-Felkin directions.

According to still further features in the described preferred embodiments the aliphatic ketone donor is selected from a group consisting of acetone, fluoroacetone, chloroacetone, 2-butanone, 3-pentanone, 2-pentanone, and dihydroxyacetone.

According to still further features in the described preferred embodiments the aldehyde acceptor is selected from a group represented by the following formulae:

and

According to still further features in the described preferred embodiments the catalytic antibody is secreted by hybridoma 38C2, having ATCC accession number HB 12005.

According to still further features in the described preferred embodiments the catalytic antibody is secreted by hybridoma 33F12, having ATCC accession number HB 12004.

According to still further features in the described preferred embodiments the catalytic antibody is elicited against a β-dicarbonyl group containing hapten.

According to still further features in the described preferred embodiments the carbonyl compound is selected from the group consisting of ketones and aldehydes.

According to still further features in the described preferred embodiments the carbonyl compound is selected from the group consisting of acetone, butanone, 2-heptanone, valeraldehyde, heptanal, decanal, ethyl 5-oxohexanoate, cyclopentanone, cyclohexanone and cycloheptanone.

Further according to the present invention there is provided a method of dedeuteration or detritiation of a carbonyl compound comprising the step of contacting the carbonyl compound with a catalytic antibody being capable of catalyzing an aldol addition reaction in a presence of an aqueous solution to thereby exchange at least one deuterium or tritium atom in the carbonyl compound with a hydrogen atom.

The present invention successfully addresses the shortcomings of the presently known configurations by providing a method for deuteration and tritiation of carbonyl compounds which is readily effected under room temperature and mild pH conditions.

BRIEF DESCRIPTION OF THE DRAWINGS

The invention herein described, by way of example only, with reference to the accompanying drawings, wherein:

FIG. 5 shows a lineweaver-Burk plot of the 38C2-catalyzed deuterium exchange reaction according to the present invention with three representative substrates: 2-heptanone, cycloheptanone, and heptanal. Series of reactions were carried out in a 0.1 ml solution containing the appropriate concentration of the carbonyl substrate and antibody 38C2(1.33 $\mu$M in the case of cycloheptanone and heptanal, 2.67 $\mu$M in the case of 2-heptanone) which was previously dialyzed three times against 0.1 M NaCl in $D_2O$. The reaction mixtures were kept at 25° C. for 10 minutes and then quenched with dichloromethane. The organic layer was separated and analyzed by GCMS (Chemical Ionization) where the different isotopic masses were monitored and integrated. All kinetic parameters are calculated per exchange of one deuterium atom. No background reactions could be detected under these conditions.

DESCRIPTION OF THE PREFERRED EMBODIMENTS

The present invention is of a catalytic antibody which can be effectively used for deuteration and/or tritiation of carbonyl compounds. Specifically, the present invention can be used for synthesizing deuterated and tritiated compounds for chemical, biochemical, biomedical and industrial research, structure determination and organic and biosynthetic mechanism studies.

The principles and operation of a catalytic antibody according to the present invention and the use thereof for deuteration of carbonyl compounds may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The recent introduction of the new concept of reactive immunization represents a major milestone in the field of catalytic antibodies. In reactive immunization one immunizes with compounds that are highly reactive in order to create a chemical reaction during the binding of the antigen to the antibody. The same reaction becomes part of the mechanism of the catalytic event. In other words, the antibodies are elicited against a chemical reaction, instead of a stable transition state analog. This idea is schematically presented in FIG. 1 for a mechanism of trapping the essential ε-amino group of a lysine residue in the antibody's binding pocket by using a 1,3-diketone group containing hapten 2.

Figure 1:
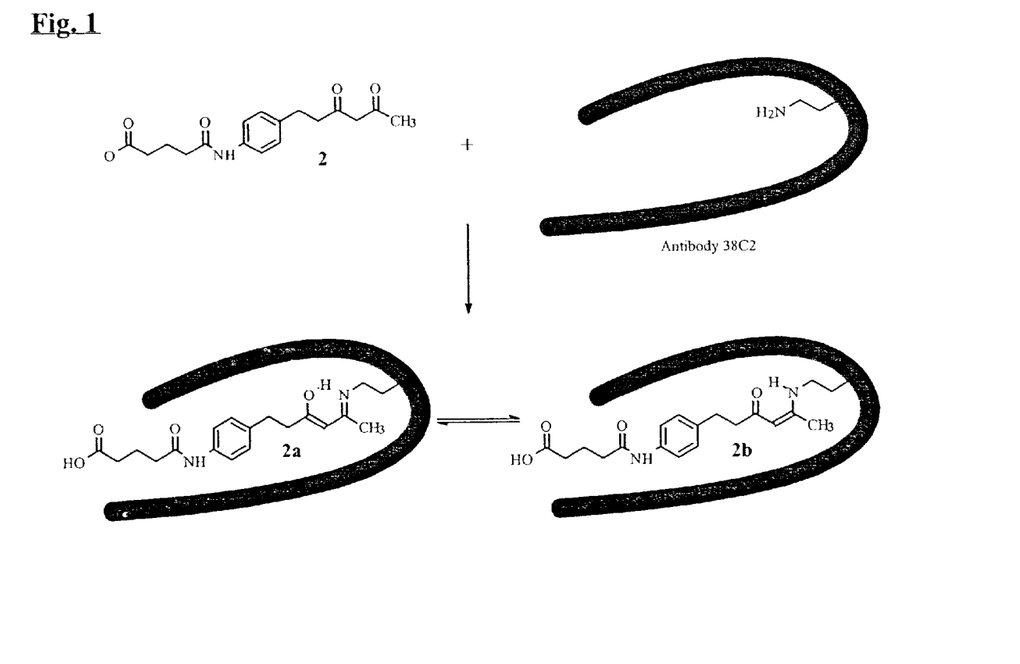
FIG. 1 shows a mechanism of trapping an essential ε-amino group of a lysine residue in an antibody's binding pocket by using a 1,3-diketone group containing hapten.
Figure 2:
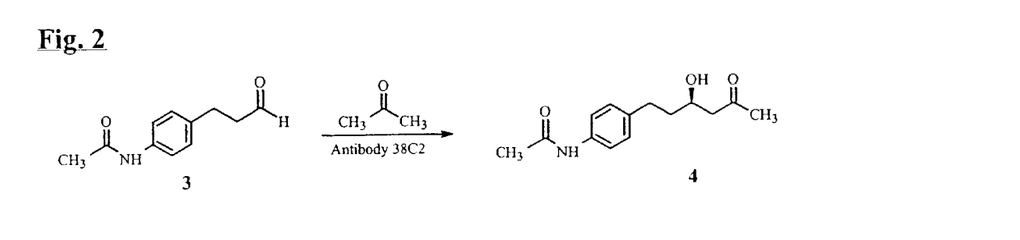
FIG. 2 shows addition of acetone to aldehyde to produce β-hydroxy ketone.

The power of this concept has been demonstrated in the past by eliciting antibodies that catalyze the aldol condensation using the same mechanism as the class I aldolases do. To this end, see WO 96-US20052 and U.S. Pat. No. 5,733,757, to Barbas, III et al., the latter is incorporated by reference as if fully set forth herein. The latter antibodies utilize the ε-amino group of a lysine residue in the active site to form a Schiff base with the donor substrate, which activates it as an enamine nucleophile that reacts with the aldol acceptor to form a new C—C bond. The resultant Schiff base is then hydrolyzed to release the aldol product. Hapten 2 in FIG. 1 is designed to trap the essential lysine residue inside the antibody's active site and, at the same time, to create the appropriate binding site that will facilitate this bimolecular reaction by overcoming the entropic barrier. The driving force for the reaction of such a hapten with the antibody is the formation of a stable covalent bonding between the hapten and the primary amine residue in the binding pocket (FIG. 1). The resultant conjugated enamine can be identified using its characteristic absorption at 316 nm. Two anti-1,3-diketone antibodies, termed 38C2 and 33F12, were proved to bind covalently to their hapten. As shown in FIG. 2, both antibodies catalyze the addition of acetone to aldehyde 3 to produce β-hydroxy ketone 4, exhibiting Michaelis-Menten kinetics.

Figure 3:
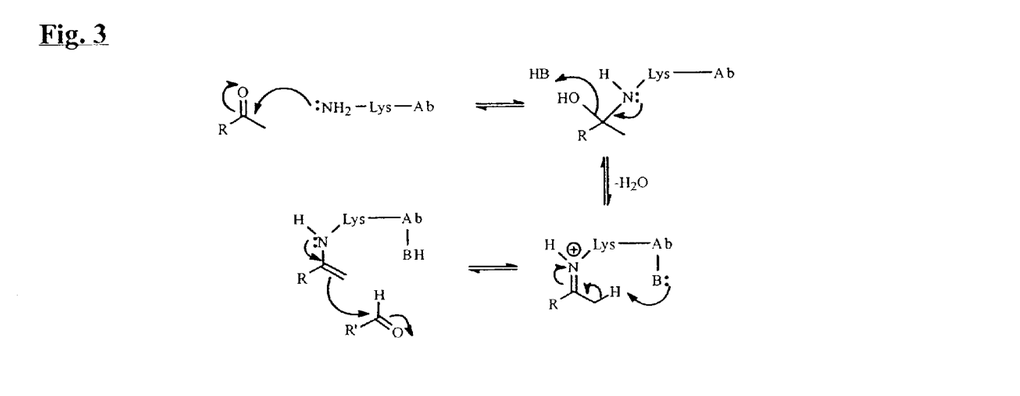
FIG. 3 shows the mechanism of aldol condensation inflicted by antibody 38C2.

As shown in FIG. 3, the mechanism by which catalytic lysine antibodies, such as antibodies 38C2 and 33F12, promote the aldol condensation involves activation of the carbonyl donor in the form of an enamine intermediate. In the absence of a proper carbonyl acceptor this enamine can only hydrolyze back to its carbonyl precursor. This carbonyl-enamine equilibrium provides the means for efficient exchange of the α-hydrogens with the water hydrogens inside the antibody's binding site.

While conceiving the present invention, it was reasoned that the aldolase antibodies (10) 38C2 and 33F12 could create an unprecedented opportunity to enable efficient deuteration of a variety of carbonyl compounds, including, but not limited to, ketones and aldehydes, since the deuterium or tritium exchange reaction could be carried out under neutral conditions. Since these catalytic antibodies were produced via the novel technique of reactive immunization, they are designed to be efficient catalysts and yet, unlike most enzymes, work on a broad scope of substrates (11). Although the antibody can catalyze aldol condensation of small size aldehydes, long chain or bulky aldehyde substrates will not undergo this condensation reaction yet, they are expected to exchange their α-hydrogens. In fact, protons exchange is expected to occur for any ketone group or aldehyde group containing substrate.

Figure 4:
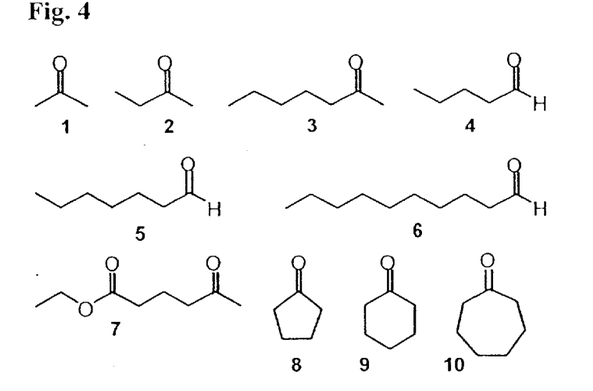
FIG. 4 shows ten representative ketones and aldehydes employed while reducing the present invention to practice.

To verify these assumptions, while reducing the present invention to practice, the deuterium exchange reaction catalyzed by the 38C2 antibody was studied with ten representative ketones and aldehydes, 1–10 (FIG. 4).

The issue of kinetic analyses of these catalytic reactions and structure determination of the deuterium labeled products is not trivial. The common chromatographic methods, such as HPLC, used to monitor protein-catalyzed organic reactions that are carried out at very low concentrations, are not applicable to isotope exchange reactions. Work at low concentrations, at the range of the antibody's Km, is required in order to establish the kinetic parameters of the antibody catalyzed reaction. Consequently, alternative methods such as mass spectrometry and NMR are required. For NMR spectroscopy, deuterated substrates were used and the exchange of $^2H$ and $^1H$ was followed by $^1H$-NMR. This allows for monitoring the reaction in real time in the presence of antibody and buffer solution. The experiments were carried out in relatively high substrate concentrations, due to the limited sensitivity of the instrument. Most experiments employed deuterated acetonitrile as an internal standard that enables one to quantify the results. It will be appreciated that the employment of NMR techniques is valuable not only for kinetic studies but also for determining the product's stereochemistry as well as the regio, chemo- and enantioselectivity of the reaction.

All reactions were carried out in $D_2O$ under neutral conditions (pD 7.4) in the presence of catalytic amounts of the commercially available 38C2 antibody [4].

Figure 5:
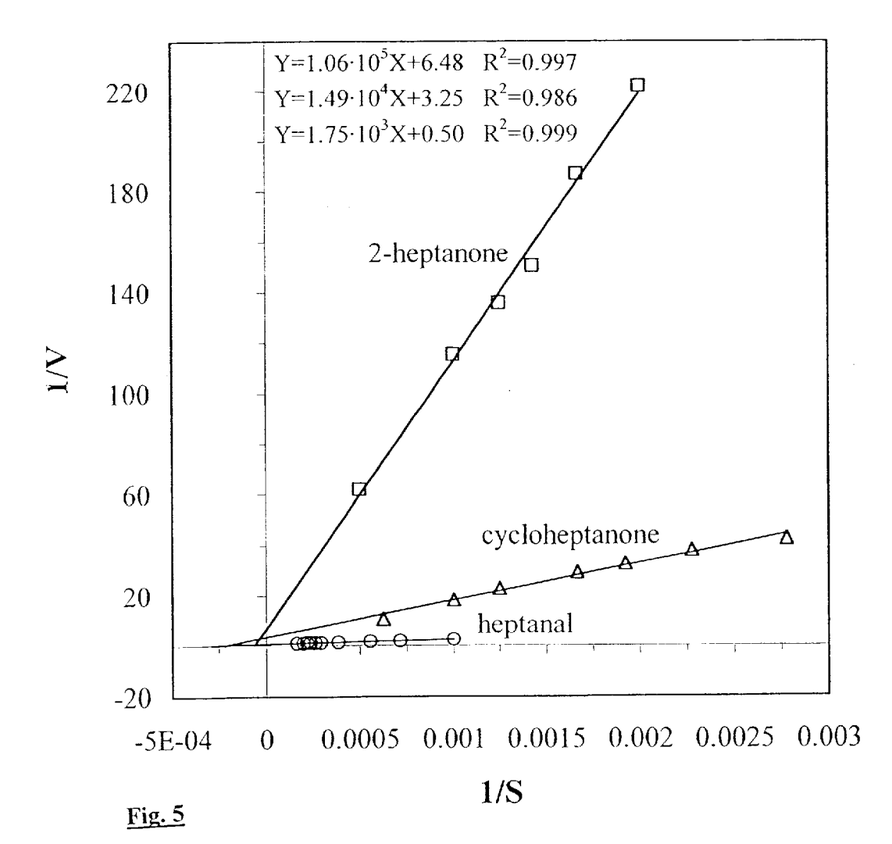

The exchange reaction was followed either by mass spectrometry (GCMS.) or by $^1H$-NMR. The high sensitivity of the GCMS method with respect to substrate concentration allowed for determination of the kinetic parameters of these reactions ($K_m$ and $k_{cat}$) using Lineweaver-Burk analysis. These measurements are presented in Table 1 hereinunder and FIG. 5.

TABLE 1

| Substrate | $k_{cat}$ (min$^{-1}$)[a] | $K_M$ (mM) | $k_{cat}/k_{un}$ |
|---|---|---|---|
| Acetone, 1 | 2.6 | | |
| Butanone, 2 | 3.1 | | |
| 2-Heptanone, 3 | 3.5 | 16 | $6.94 \times 10^7$ |
| Valeraldehyde, 4 | 3.4 | | b |

TABLE 1-continued

| Substrate | $k_{cat}$ (min$^{-1}$)[a] | $K_M$ (mM) | $k_{cat}/k_{un}$ |
|---|---|---|---|
| Heptanal, 5 | 45.2 | 3.5 | b |
| Decanal, 6 | 4.0 | 0.68 | |
| Ethyl 5-oxohexanoate, 7 | 0.8 | | b |
| Cyclopentanone, 8 | 6.1 | | |
| Cyclohexanone, 9 | 194.0 | 5.2 | $5.9 \times 10^8$ |
| Cycloheptanone, 10 | 13.9 | 4.6 | $1.1 \times 10^8$ |

Kinetic data for antibody 38C2-catalyzed deuteration of ketones and aldehydes.
[a] All kinetic parameters refer to the exchange of one hydrogen atom.
[b] No background rate ($k_{un}$) could be determined due to complete loss of starting material before any exchange product could be detected.

In all cases studied by GCMS, the deuterium exchange reaction followed Michaelis-Menten kinetics and was effectively inhibited by acetylacetone (10). Although all NMR measurements were carried out under substrate saturation conditions (allowing only for determination of $V_{max}$ and $k_{cat}$, Table 1, above), as further detailed hereinunder, this method provided useful information about the regioselectivity of the reaction in the cases of non-symmetrical ketones and chemoselectivity with polyfunctional carbonyl compounds.

The results summarized in Table 1 above highlight the synthetically useful range of substrates accepted by antibody 38C2. Although there are a few reported cases of an enzyme-catalyzed exchange of α protons under mild conditions, practically all of them were limited to very few substrates (12).

It is difficult to assess the actual rate enhancement of the deuteration reaction because of the controversy in the literature over the uncatalyzed background rates (13). In the present case it was necessary to run the uncatalyzed reaction for five months in order to detect measurable quantities of products (14). Thus, even taking the most generous estimate for the uncatalyzed rates, the rate enhancement in the deuteration reaction is approximately $10^8$–$10^9$ fold.

The efficient antibody-catalyzed deuteration of aldehydes (Table 1) is of particular synthetic significance on grounds of the chemical instability of aldehydes relative to ketones.

The aldehyde substrates employed herein were found to be incompatible even with the mild reaction conditions (room temperature, aqueous medium, neutral pH) over the prolonged periods of time required for detecting the uncatalyzed reaction. Similarly, even with a more stable substrate, such as keto-ester 7, one failed to detect any product of the uncatalyzed reaction due to consumption of the substrate in various side reactions during its long standing in the aqueous medium.

Prior observations with antibody 38C2-catalyzed aldol, retrograde aldol, and decarboxylation reactions (11, 15) suggest that all of these reactions involve formation of an intermediate Schiff base with the lysine residue within the antibody's active site.

Figure 6:
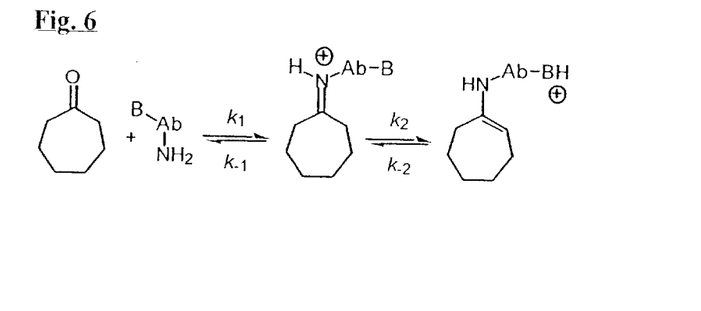
FIG. 6 shows a multistep deuterium exchange reaction in which every proton is exchanged individually in a series of equilibria, exemplified for cycloheptanone.

Therefore, it is likely to assume that the deuterium exchange reaction also involves a multistep process in which every proton is exchanged individually in a series of equilibria. As shown in FIG. 6 for cycloheptanone, this assumption was proven correct.

An important question is what are the relative rates of the two main steps, i.e., formation of the protonated Schiff base and tautomerization of the latter to an enamine. If the first step is fast relative to the second step, the expected kinetic behavior of the entire process is that of four consecutive pseudo first order reactions with the formation and disappearance of all partially deuterated products, $d_1$, $d_2$, and $d_3$. Alternatively, if the second step is faster than the first one, no partially deuterated intermediates are expected to be observed in the reaction.

Figure 7:
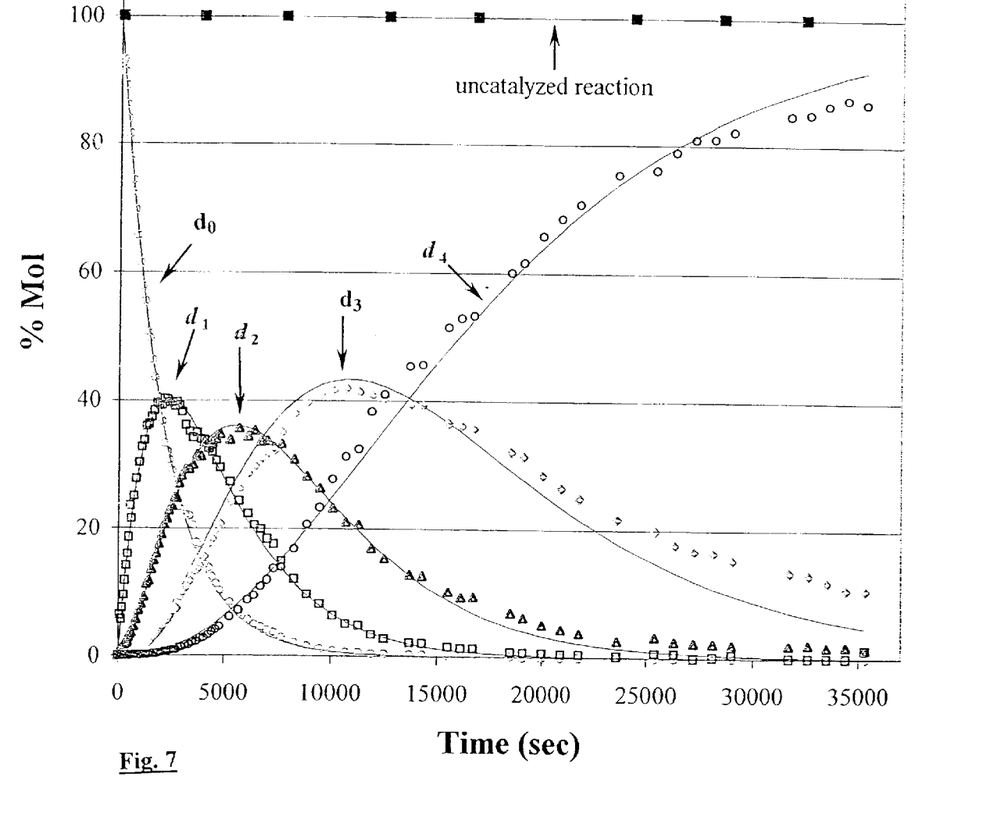
FIG. 7 shows deuteration of cycloheptanone catalyzed by antibody 38C2. All data points were obtained from time-resolved GCMS measurements. The calculated curves are based on a four-step series of consecutive first-order reactions using a single rate constant multiplied by the appropriate statistical factor.

To check this issue the exchange reaction of cycloheptanone was monitored by GCMS (FIG. 7). The data shown in FIG. 7 fit well with a kinetic model of four consecutive first order reactions, where each step is independent of the others (16). A single rate constant with statistical corrections describe the seemingly complicated array of data. Thus, the first-order rate constant (k) related to the first step (monodeuteration of cycloheptanone to produce cycloheptanone-$d_1$) was easily determined from the exponential curve (describing the disappearance of cycloheptanone-$d_0$). The rate constant for the next step (formation of cycloheptanone-$d_2$) is 3/4k. The rate constant for the third step (formation of cycloheptanone-d3) is 1/2k and the rate constant for the fourth step (formation of cycloheptanone-$d_4$) is 1/4k.

The excellent agreement between the experimental data and calculated curves confirms that the exchange reaction occurs in a stepwise manner. Also, this agreement justifies the assumption that the second-order isotope effect can be neglected.

Thus, referring to FIG. 7, $k_{-1}$ is large compared with $k_2$ and the process corresponding to $k_1/k_{-1}$ can be treated as a pre-equilibrium.

A similar behavior has been observed by Westheimer in the acetoacetate decarboxylase-catalyzed de-deuteration reaction with acetone-$d_6$(17).

The regioselectivity of the deuterium exchange at the α versus α' positions of non-symmetrical ketones is of particular interest because it enables one to synthesize specific, predesigned, deuterated and tritiated compounds. With linear ketones, such as 2-butanone, the regioselectivity is known to depend on the nature of the catalyst used.

The exchange of the methylene hydrogen is generally preferred over the methyl hydrogen under strong acid catalysis ($k_{CH2}/k_{CH3}$=2.5) and under neutral conditions ($k_{CH2}/k_{CH3}$=1.6). In contrast, under strong base catalysis, the opposite regioselectivity is observed ($k_{CH2}/(k_{CH3}$=0.7) (18).

Other ratios within this range ($k_{CH2}/k_{CH3}$=1.0–2.0) have been reported for a variety of weak acid and base catalysts, such as acetate buffer solutions (9a, 19).

Figure 8A:
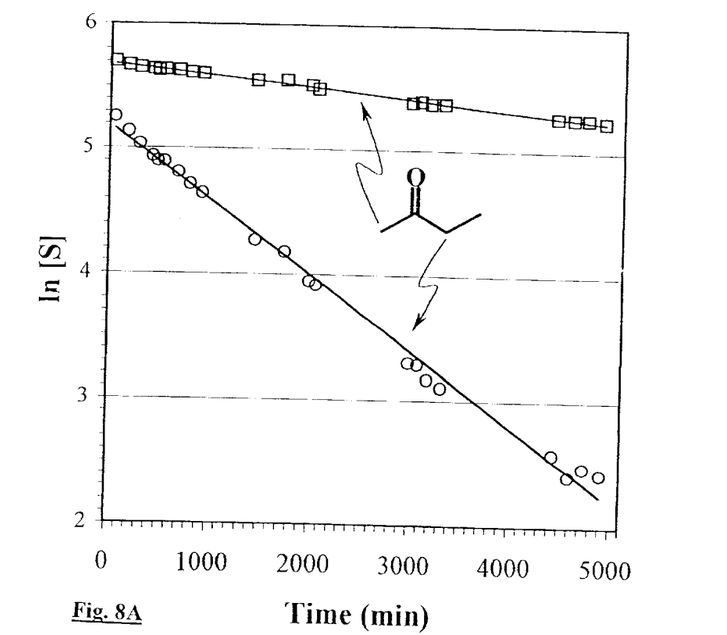
FIGS. 8A and 8B show regioselective deuteration of butanone and ethyl 5-oxohexanoate, respectively. An aqueous solution ($D_2O$, 0.55 ml) containing NaCl (0.1 M), ketone substrate (0.1 M) and antibody 38C2(13.3 $\mu$M, which has been dialyzed three times against 0.1 M NaCl in $D_2O$) was placed in an NMR tube at 25° C. and the reaction was monitored by $^1H$ NMR.
Figure 8B:
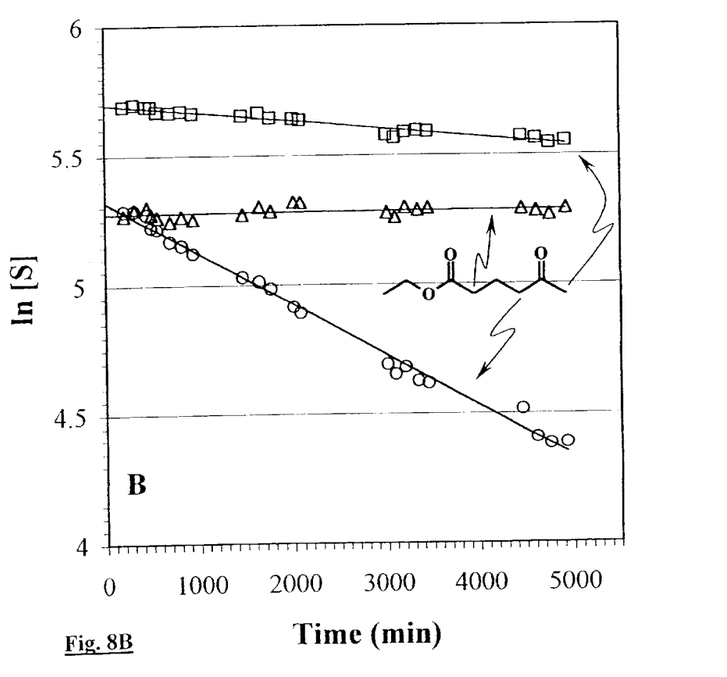

It was found herein that the antibody-catalyzed exchange of 2-butanone at neutral pH is significantly more regioselective than the highest value reported for acid catalysis ($k_{CH2}/k_{CH3}$=3.2, FIG. 8A). With larger and significantly non-symmetrical substrates, such as ethyl 5-oxohexanoate, 7, the discrimination in favor of the methylene is even higher ($k_{CH2}/k_{CH3}$=4.7, FIG. 8B).

Beyond the potential practical applications of this reaction in regioselective isotopic labeling of organic compounds, these findings point to two important features of the antibody-catalyzed exchange reaction.

First, although the reaction is carried out under neutral aqueous conditions, its mechanism resembles that of a typical acid-catalyzed exchange reaction. This observation is consistent with the formation of a protonated Schiff base intermediate with the lysine residue in the antibody active site (I in FIG. 9) followed by a reversible rearrangement to the corresponding enamine (II in FIG. 9).

Second, the regioselectivity under antibody catalysis is higher than that expected for simple acid catalysis. Considering this observation together with the known structure of the hapten used to raise antibody 38C2(10), one would expect that the Schiff-base intermediate, I (FIG. 9), has a non-symmetrical orientation within the binding site. Thus, the methyl group is located deep in the binding pocket and the longer alkyl chain is positioned away from the lysine group towards the solvent.

Figure 9:
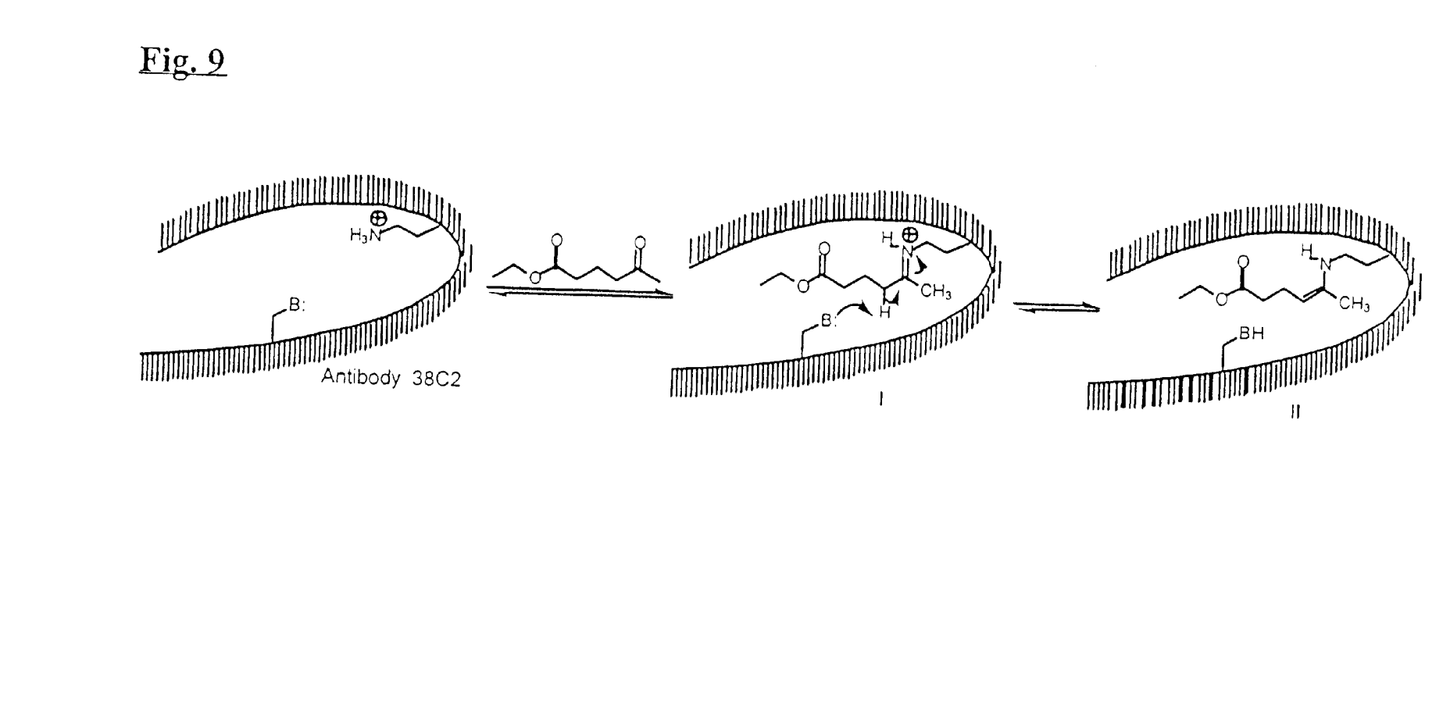
FIG. 9 shows the formation of a protonated Schiff base intermediate with the lysine residue in the antibody active site followed by a reversible rearrangement to the corresponding enamine.

The results shown herein suggest that a general base residue located between the lysine group and the solvent is responsible for the regioselective deprotonation (FIG. 9). That general base may preferentially deprotonate the α' position rather than the a position either directly (as shown in FIG. 9) or via a relay of water molecules.

This hypothesis is reinforced by the crystal structure of a close homologue of antibody 38C2: the aldolase antibody, 33F12 (20). That structure reveals a glutamate (Glu-H44) residue whose carboxylate is positioned approximately 7 angstrom away from the active site lysine (Lys-H93) nitrogen towards the solvent. It is also plausible that an active site tyrosine (e.g., Tyr-L41) may act as a general base in this reaction (11c).

An interesting observation that further supports this hypothesis is the absolute inertness of 3,3-dimethylbutan-2-one to the 38C2-catalyzed deuterium exchange reaction (data not shown).

In conclusion, it is shown herein that antibody 38C2 catalyzes the deuterium exchange reaction with a broad variety of ketones and aldehydes. The catalytic rates and rate-enhancement values represent the highest values ever observed with catalytic antibodies. Such values are reminiscent of the efficiency of many natural enzymes.

Thus, according to the present invention there is provided a method of deuteration or tritiation of a carbonyl compound.

As used herein in the specification and in the claims section below, the term "carbonyl compound" refers to a chemical including at least one carbonyl group. The carbonyl compound according to the present invention can be a ketone or aldehyde, i.e., including a ketone group or an aldehyde group. Examples include, but are not limited to, acetone, butanone, 2-heptanone, valeraldehyde, heptanal, decanal, ethyl 5-oxohexanoate, cyclopentanone, cyclohexanone and cycloheptanone.

The method according to the present invention is effected by contacting, in aqueous solution enriched with an isotopically enriched water molecule, the carbonyl compound with a catalytic antibody which is capable of catalyzing an aldol addition reaction, to thereby exchange at least one hydrogen atom in the carbonyl compound with a deuterium or tritium atom.

As used herein in the specification and in the claims section below, the term "isotopically enriched water molecule" refers to deuterium hydrogen oxide (DHO), dideuterium oxide ($D_2O$) and, tritium hydrogen oxide (THO), ditritium oxide ($T_2O$), and/or deuterium tritium oxide (DTO)

As used herein in the specification and in the claims section below, the term "antibody" refers to any of several classes of structurally related proteins, also known as immunoglobulins, that function as part of the immune response of an animal, which proteins include IgG, IgD, IgE, IgA, IgM and related proteins. This term further relates to chimeric immunoglobulins which are the expression products of fused genes derived from different species. These terms further relate to immunologically active derivatives of the above proteins, including, but not limited to, an $F(ab')_2$ fragment, an Fab fragment, an Fv fragment, a heavy chain, a light chain, an unassociated mixture of a heavy chain and a light chain, a heterodimer consisting of a heavy chain and a light chain, a catalytic domain of a heavy chain, a catalytic domain of a light chain, a variable fragment of a light chain, a variable fragment of a heavy chain, and a single chain variant of the antibody. Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. The antibody according to the present invention could also be a "humanized" antibody, in which, for example, animal (say murine) variable regions are fused to human constant regions, or in which murine complementarity-determining regions are grafted onto a human antibody structure (21). Unlike, for example, animal derived antibodies, "humanized" antibodies often do not undergo an undesirable reaction with the immune system of the subject. The terms "sFv" and "single chain antigen binding protein" refer to a type of a fragment of an immunoglobulin, an example of which is sFv CC49 (22).

As used herein, the term "humanized antibodies" also reads on antibodies produced by non-human cells or organisms genetically modified to include nucleic acid sequences encoding a functional portion of the human immune system, wherein the resulting antibodies are substantially identical to human antibodies in that they are encoded by human derived genes. However, the term "antibody", as used herein, also relates to any entity linked to an antibody portion including the antibody binding pocket.

As used herein and in the claims, the term "animal" refers to any organism with an immune system.

According to a preferred embodiment of the present invention the catalytic antibody is capable of catalyzing an aldol addition reaction between an aliphatic ketone donor, such as, but not limited to, acetone, fluoroacetone, chloroacetone, 2-butanone, 3-pentanone, 2-pentanone, and dihydroxyacetone, and an aldehyde acceptor. The catalytic antibody according to the present invention is characterized by having a lysine with an $\epsilon$-amino group, and it is subject to inhibition with a molecule containing a $\beta$-dicarbonyl group (e.g., a $\beta$-diketone group) by formation of a complex between the $\beta$-dicarbonyl group and the $\epsilon$-amino group of the lysine of the catalytic antibody.

According to another preferred embodiment of the present invention, the above complex is a stable covalent vinylogous amide, a conjugated enamine and a Schiff base.

According to yet another preferred embodiment, the antibody controls the diastereofacial selectivity of the aldol addition reaction in both Cram-Felkin and anti-Cram-Felkin directions.

According to yet another preferred embodiment, the aldehyde acceptor is selected from a group represented by the following formulae:

and

CH$_3$—CO—NH—(C$_6$H$_6$)—CH$_2$—CH$_2$—C(=O)—H which are described in detail in U.S. Pat. No. 5,733,757.

The antibody according to the present invention is preferably secreted by hybridoma 38C2, having ATCC accession number HB 12005 or hybridoma 33F12, having ATCC accession number HB 12004.

The antibody according to the present invention is preferably elicited against a $\beta$-dicarbonyl group containing hapten, preferably, a $\beta$-diketone group containing hapten.

Methods for the generation and selection of monoclonal antibodies are well known in the art, as summarized for example in reviews such as Tramontano and Schloeder, Methods in Enzymology 178, 551–568, 1989. The $\beta$-dicarbonyl group containing hapten may be used to generate antibodies in vitro, by, for example, phage display techniques. More preferably, the $\beta$-dicarbonyl group containing hapten will be used to elicit antibodies in vivo. In general, a suitable host animal is immunized with the hapten of choice. Advantageously, the animal host used will be a mouse of an inbred strain. Animals are typically immunized with a mixture comprising a solution of the hapten in a physiologically acceptable vehicle, and any suitable adjuvant, which achieves an enhanced immune response to the hapten. By way of example, the primary immunization conveniently may be accomplished with a mixture of a solution of the hapten and Freund's complete adjuvant, the mixture being prepared in the form of a water in oil emulsion. Typically the immunization may be administered to the animals intramuscularly, intradermally, subcutaneously, intraperitoneally, into the footpads, or by any appropriate route of administration. The immunization schedule may be adapted as required, but customarily involves several subsequent or secondary immunizations using a milder adjuvant such as Freund's incomplete adjuvant. Antibody titers and specificity of binding to the hapten can be determined during the immunization schedule by any convenient method including by way of example radioimmunoassay, or enzyme linked immunoassay. Antibody activity assays can be based on detection of the reaction product of the catalytic reaction involved, and in terms of catalytic efficiency. Antibody activity assays based on the detection of reaction products or on the disappearance of substrate may conveniently be followed by methods described hereinabove. When suitable antibody titers are achieved, antibody producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multiwell plates, and the culture supernatants are screened to identify cultures containing antibodies that recognize the hapten of choice. Hybridomas that secrete antibodies that recognize the hapten of choice are cloned by limiting dilution and expanded, under appropriate culture conditions. Monoclonal antibodies are purified and characterized in terms of immunoglobulin type, binding affinity and in terms of efficiency of catalysis.

Specific details relating to the elicitation and production of the antibodies used in the method of deuteration and tritiation of carbonyl compounds according to the present invention are found in U.S. Pat. No. 5,733,757, to Barbas, III et al., which is incorporated by reference as if fully set forth herein.

It will be appreciated by one ordinarily skilled in the art, that a reverse method, in which a carbonyl compound is dedeuterated or detritiated is enabled by the specification. Such a method, is effected, according to the present invention, by contacting the carbonyl compound with a catalytic antibody being capable of catalyzing an aldol addition reaction in a presence of an aqueous solution to thereby exchange at least one deuterium or tritium atom in the carbonyl compound with a hydrogen atom.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

LIST OF CITED REFERENCES

1. Wong, C.-H.; Whitesides, G. M. "Enzymes in Synthetic Organic Chemistry", Pergamon, Oxford, UK, 1994.
2. (a) Schultz, P. G.; Lerner, R. A. Science 1995, 269, 1835. (b) Keinan, E. Lerner, R. A. Israel J. Chem. 1996, 36, 113. (c) Lerner, R. A.; Benkovic, S. J.; Schultz, P. G. Science 1991, 252, 659. (d) Thomas, N. R. Na Rep. 1996, 479.
3. (a) Charbonnier, J.-P.; Golinelli-Pimpaneau, B.; Gigant, B.; Tawfik, D. S.; Chap, R.; Schindler, D. G.; Kim, S.-H.; Green, B. S.; Eshhar, Z.; Knossow, M. Science 1997, 275, 1140; (b) Wedemayer, G. J.; Patten, P. A.; Wang, L. H.; Schultz, P. G.; Stevens, R. C. Science 1997, 276, 1665.
4. Aldrich catalog #47,995-0.
5. (a) Gassman, P. G.; Aue, D. H.; Patton, D. S. J. Am. Chem. Soc. 1968, 90, 7271. (b) Kinstle, T. H.; Chapman, O. L.; Sung, M. J. Am. Chem. Soc. 1968, 90, 1227.
6. (a) Seibl J.; Gaumann, T. Helv. Chim. Acta 1963, 46, 2857. (b) Weinberg, D. S.; Djerassi, C. J. Org. Chem. 1966, 31, 115.
7. (a) Frejaville, G.; Jullien, J. French Pat. 1,424,496, 1964; Chem. Abst. 1966, 65, 10169. (b) Mislow, K.; Glass, M. A. W.; Hopps, H. B.; Simon, E.; Wahl, Jr., G. H. J. Am. Chem. Soc. 1964, 84, 1710. (c) Senn, M.; Richter, W. J.; Burlingame, A. L. J. Am. Chem. Soc. 1965, 87, 680. (d) Albert, D. K.; Meyerson, S. Analyt. Chem. 1967, 39, 1904.
8. Even with weak bases such as tertiary amines the exchange reaction with aldehydes results in a loss of starting material, requires much deuterium oxide and gives only an asymptotic approach to isotopic purity: Kirmse, W.; von-Scholz, H.-D.; Arold, H. Ann. 1968, 22, 711.
9. (a) Hine, J.; Mulders, J.; Houston, J. G.; Idoux, J. P. J. Org. Chem. 1967, 32, 2205. (b) Hine, J.; Menon, B. C.; ulders, J.; Idoux, J. P. J. Org. Chem. 1967, 32, 3850.
10. Wagner, J.; Lerner, R. A.; Barbas III, C. F. Science 1995, 270, 1797.
11. (a) Zhong, G.; Hoffmann, T.; Lerner, R. A.; Danishefsky, S.; Barbas III, C. F J. Am. Chem. Soc. 1997, 119, 8131. (b) List, B.; Shabat, D.; Barbas III, C. F.; Lerner, R. A. Chemistry Eur. J. 1998, 4, 881. (c) Hoffmann, T.; Zhong, G.; List, B.; Shabat, D.; Anderson, J.; Gramatikova, S.; Lerner, R. A.; Barbas, C.F. III J. Am. Chem. Soc. 1998, 120, 2768.
12. Pyruvic acid was deuterated using oxaloacetate decarboxylase: Kosicki, G. W. Biochem. 1968, 7, 4310. Acetone and butanone were deuterated using acetoacetate decarboxylase under slightly acidic conditions (pH 5.9); (a) Tagaki, W.; Westheimer, F. H. Biochem. 1968, 7, 901. (b) Hammons, G.; Westheimer, S. H.; Nakaoka, K.; Kluger, R. J. Am. Chem. Soc. 1975, 97, 1568. Dihydroxyacetone phosphate was tritiated using Rabbit muscle aldolase: (a) Rose, I. A.; Rieder, S. V. J. Biol. Chem. 1958, 231, 315. (b) Pratt, R. F. Biochem. 1977, 16, 3988. Enantioselective deuteration of cyclohexanone acid was achieved with acetoacetate decarboxylase: Benner, S. A.; Rozzell Jr., J. D. J. Am. Chem. Soc. 1981, 103, 993. For other examples of substrate specific deuterium exchange reactions, see Grady, S. R.; Dekker, E. E. Biochim. Biophys. Acta 1979, 568, 234 and references cited therein.
13. (a) Warkentin, J.; Cox. R. A. J. Org. Chem. 1968, 33, 1301. (b) Hine, J.; Hampton, K. G.; Menon, B. C. J. Am. Chem. Soc. 1967, 89, 2664. (c) Jullien, J; Thoi-Lai, N. Bull. Soc. Chim. Fr. 1970, 11, 3948.
14. The rate of the uncatalyzed reaction was determined by averaging the results of five experiments for each substrate. All reaction mixtures, containing the appropriate substrate (200 $\mu$M) and NaCl (0.1 M) in $D_2O$ (0.1 mL), were monitored by GCMS-CI. Approximately 1–2% yield was observed after 5 months at 25° C.
15. Bjornestedt, R.; Zhong, G.; Lemer, R. A.; Barbas, C. F. III J. Am. Chem. Soc. 1996, 118, 11720.
16. Benson, S. "The Foundations of Chemical Kinetics", McGraw-Hill, New York, N.Y, 1960, pp 39.
17. Hammons, G. H.; Westheimer, F. H.; Nakaoka, K.; Kluger, R. J. Am. Cher Soc. 1975, 97, 1568.
18. Rappe, C. Acta Chem. Scand. 1966, 20, 2236.
19. Warkentin, J. A.; Tee, O. S. J. Am. Chem. Soc. 1966, 88, 5540.
20. Barbas, C. F. III; Heine, A.; Zhong, G.; Hoffmann, T.; Gramatikiva, S.; Bjornestedt, R.; List, B.; Anderson, J.; Stura, E.; Wilson, I. A.; Lerner, R. A. Science 1997, 278, 2085.
21. Wilder, R. B. et al., J. Clin. Oncol., 14:1383–1400, 1996.
22. Larson, S. M. et al., Cancer, 80:2458–68, 1997.

What is claimed is:

1. A method of deuterating or tritiating a carbonyl compound, the method comprising the steps of contacting the carbonyl compound with a catalytic antibody for catalyzing an aldol addition reaction in a presence of an aqueous solution enriched with an isotopically enriched water molecules, thereby exchanging at least one hydrogen atom in said carbonyl compound with a deuterium or tritium atom and obtaining a deuterated or tritiated carbonyl compound.

2. The method of claim 1, wherein said isotopically enriched water molecule is selected from the group consisting of deuterium hydrogen oxide, dideuterium oxide, tritium hydrogen oxide, ditritium oxide and deuterium tritium oxide.

3. The method of claim 1, wherein said catalytic antibody is capable of catalyzing said aldol addition reaction between an aliphatic ketone donor and an aldehyde acceptor.

4. The method of claim 1, wherein said catalytic antibody is characterized by having a lysine with an $\epsilon$-amino group in its binding pocket.

5. The method of claim 4, wherein said catalytic antibody is subject to inhibition with a molecule containing a $\beta$-dicarbonyl group by formation of a complex between said $\beta$-dicarbonyl group and the $\epsilon$-amino group of said lysine of said catalytic antibody.

6. The method of claim 5, wherein said complex is selected from the group consisting of a stable covalent vinylogous amide, a conjugated enamine and a Schiff base.

7. The method of claim 1 wherein said catalytic antibody controls the diastereofacial selectivity of said aldol addition reaction in both Cram-Felkin and anti-Cram-Felkin directions.

8. The method of claim 3, wherein said aliphatic ketone donor is selected from a group consisting of acetone, fluoroacetone, chloroacetone, 2-butanone, 3-pentanone, 2-pentanone, and dihydroxyacetone.

9. The method of claim 3, wherein said aldehyde acceptor is selected from a group represented by the following formulae:

AcNH—(C$_6$H$_6$)—CH$_2$—CH(↑CH$_3$)—C(=O)—H,

AcNH—(C$_6$H$_6$)—CH$_2$—CH(↓CH$_3$)—C(=O)—H and

CH$_3$—CO—NH—(C$_6$H$_6$)—CH$_2$—CH$_2$—C(=O)—H.

10. The method of claim 1, wherein said catalytic antibody is secreted by hybridoma 38C2, having ATCC accession number HB 12005.

11. The method of claim 1, wherein said catalytic antibody is secreted by hybridoma 33F12, having ATCC accession number HB 12004.

12. The method of claim 1, wherein said catalytic antibody is elicited against a β-dicarbonyl group containing hapten.

13. The method of claim 1, wherein said carbonyl compound is selected from the group consisting of molecules containing ketones and aldehydes.

14. The method of claim 1, wherein said carbonyl compound is selected from the group consisting of acetone, butanone, 2-heptanone, valeraldehyde, heptanal, decanal, ethyl 5-oxohexanoate, cyclopentanone, cyclohexanone and cycloheptanone.

15. A method of dedeuterating or detritiating a carbonyl compound, the method comprising the steps of contacting the carbonyl compound with a catalytic antibody for catalyzing an aldol addition reaction in a presence of an aqueous solution, thereby exchanging at least one deuterium or tritium atom in said carbonyl compound with a hydrogen atom and obtaining dedeuterated or detritiated carbonyl compound.

* * * * *